(12) United States Patent
Gurtner et al.

(10) Patent No.: US 9,655,967 B2
(45) Date of Patent: May 23, 2017

(54) INHIBITION OF FOCAL ADHESION KINASE FOR CONTROL OF SCAR TISSUE FORMATION

(71) Applicant: The Board of Trustees of the Leland Stanford Junior University, Palo Alto, CA (US)

(72) Inventors: Geoffrey C. Gurtner, Palo Alto, CA (US); Michael T. Longaker, Stanford, CA (US); Victor W. Wong, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 374 days.

(21) Appl. No.: 13/706,186

(22) Filed: Dec. 5, 2012

(65) Prior Publication Data

US 2013/0165463 A1    Jun. 27, 2013

Related U.S. Application Data

(60) Provisional application No. 61/569,102, filed on Dec. 9, 2011.

(51) Int. Cl.
*A61K 45/06* (2006.01)
*A61K 31/506* (2006.01)

(52) U.S. Cl.
CPC ............ *A61K 45/06* (2013.01); *A61K 31/506* (2013.01)

(58) Field of Classification Search
CPC .............................. A61K 31/506; A61K 45/06
USPC ....................................................... 514/275
See application file for complete search history.

(56) References Cited

U.S. PATENT DOCUMENTS 4,191,743 A * 3/1980 Klemm et al. ................ 424/445
5,741,777 A * 4/1998 Grinnell et al. .............. 424/484
2002/0122795 A1* 9/2002 Paller .......................... 424/130.1
2008/0033334 A1 2/2008 Gurtner et al.
2009/0214474 A1* 8/2009 Jennings ...................... 424/85.7
2011/0009332 A1* 1/2011 Rossini ........................ 514/18.6

OTHER PUBLICATIONS

Slack Davis et al. J. Biol. Chem 2007, 282: 14845-14852.*
Aarabi; et al. "Mechanical load initiates hypertrophic scar formation through decreased cellular apoptosis", Faseb J (Oct. 2007), 21(12):3250-3261.
Essayem; et al. "Hair cycle and wound healing in mice with a keratinocyte-restricted deletion of FAK", Oncogene (Feb. 2006), 25(7):1081-1089.
Gurtner; et al. "Improving Cutaneous Scar Formation by Controlling the Mechanical Environment: Large Animal and Phase I Studies", Annals of Surgery (Aug. 2011), 254(2):217-225, abstract only.
Gurtner; et al. "Wound repair and regeneration", Nature (May 2008), 453(7193):314-321.
Ingber; et al. Mechanobiology and diseases of mechanotransduction Ann Med (2003), 35(8):564-577.
Jaalouk; et al. "Mechanotransduction gone awry", Nat Rev Mol Cell Biol (Jan. 2009), 10(1):63-73.
McLean; et al ."Specific deletion of focal adhesion kinase suppresses tumor formation and blocks malignant progression", Genes Dev (Dec. 2004), 18(24):2998-3003.
Parsons; et al. "Focal adhesion kinase: the first ten years", J Cell Sci (Apr. 2003), 116(Pt 8):1409-1416.
Wong; et al. "Keratinocyte- and Fibroblast-Specific FAK Signaling Critically Mediate Scar Matrix Remodeling During Supraphysiologic Loading", Academic Surgical Congress (Feb. 2011), abstract only.
Wong; et al."Erasing Langer's lines: Establishing a molecular basis for the fibrotic response to tension", Journal of American College of Surgeons (Sep. 2011), 213(3):S99.

* cited by examiner

*Primary Examiner* — Shirley V Gembeh
(74) *Attorney, Agent, or Firm* — Pamela J. Sherwood; Bozicevic, Field & Francis LLP

(57) ABSTRACT

The formation of scars at a wound site is reduced by contacting the wound site with an effective dose of an inhibitor of focal adhesion kinase (FAK) activity or expression. Blockade of FAK is sufficient to prevent mechanical and inflammatory stimuli from activating MCP-1 pathways. In addition to these chemokine-mediated mechanisms, inhibition of FAK may control fibrosis by blocking fibroblast collagen production. Pharmacologic blockade of FAK significantly reduces scar formation in vivo.

3 Claims, 4 Drawing Sheets
(4 of 4 Drawing Sheet(s) Filed in Color)

INHIBITION OF FOCAL ADHESION KINASE FOR CONTROL OF SCAR TISSUE FORMATION

GOVERNMENT SUPPORT

This invention was made with Government support under contract W81XWH-08-2-0032 awarded by the Department of Defense. The Government has certain rights in the invention.

BACKGROUND

Scars form in response to cutaneous injury as part of the natural wound healing process. Wound healing is a lengthy and continuous process, although it is typically recognized as occurring in stages. The process begins immediately after injury, with an inflammatory stage. During this stage, which typically lasts from two days to one week (depending on the wound), damaged tissues and foreign matter are removed from the wound. The proliferative stage occurs at a time after the inflammatory stage and is characterized by fibroblast proliferation and collagen and proteoglycan production. It is during the proliferative stage that the extracellular matrix is synthesized in order to provide structural integrity to the wound. The proliferative stage usually lasts about four days to several weeks, depending on the nature of the wound, and it is during this stage when hypertrophic scars usually form. The last stage is called the remodeling stage. During the remodeling stage the previously constructed and randomly organized matrix is remodeled into an organized structure that is highly cross-linked and aligned to increase mechanical strength.

Hypertrophic scar formation is a major clinical problem, which can give rise to exuberant scarring that results in permanent functional loss and the stigma of disfigurement. Clinical experience suggests that hypertrophic scarring is an aberrant form of the normal processes of wound healing. Hypertrophic scarring should be distinguished from keloid formation, the other major form of excessive scarring seen in humans. Keloids are characterized by overgrowth of fibrosis beyond the boundaries of the original injury, while hypertrophic scars do not extend beyond the original wound margins. Keloids and hypertrophic scars can also be differentiated by established histopathological criteria, which include differences in collagen density and orientation, vascularity, and other factors.

The pathophysiology of hypertrophic scar formation involves a constitutively active proliferative phase of wound healing. Scar tissue has a unique structural makeup that is highly vascular, with inflammatory cells and fibroblasts contributing to an abundant and disorganized matrix structure. The net result is that the original skin defect is replaced by a nonfunctional mass of tissue.

In both adult and fetal healing, the local wound environment interacts with the cellular components of wound healing and vice versa. The local wound environment consists of noncellular influences such as matrix components, oxygen tension, and mechanical forces. The interplay between cellular and noncellular components is complex, with constant feedback between the two during the healing process.

The inflammatory response is a normal component of the wound healing process, serving both as an immunological barrier from infection and as a stimulus for fibrosis to close the site of injury. Observations from human pathological specimens and from healing fetal wounds suggest that a robust inflammatory response may underlie the excessive fibrosis seen in hypertrophic scar formation. Mast cells, macrophages, and lymphocytes have all been implicated in this process. For example, mast cells have been shown to directly regulate stromal cell activity in vitro as well as to be strongly associated with the induction of fibrosis in vivo. Mechanical activity, age-specific changes, and delayed epithelialization have all been implicated as inciting factors for this intense inflammatory response.

A cell's external mechanical environment can trigger biological responses inside the cells and change cell behavior. Cells can sense and respond to changes in their mechanical environment using integrin, an integral membrane protein in the plasma membrane of cells, and intracellular pathways. The intracellular pathways are initiated by receptors attached to cell membranes and the cell membrane that can sense mechanical forces. For example, mechanical forces can induce secretion of cytokines, chemokines, growth factors, and other biologically active compounds that can increase or trigger the inflammatory response. Such secretions can act in the cells that secrete them (intracrine), on the cells that secrete them (autocrine), on cells surrounding the cells that secrete them (paracrine), or act at a distance from the point of secretion (endocrine). Intracrine interference can alter cell signaling, which can in turn alter cell behavior and biology including the recruitment of cells to the wound, proliferation of cells at the wound, and cell death in the wound. In addition, the extracellular matrix may be affected.

Following cutaneous injury, endothelial damage and platelet aggregation occur resulting in the secretion of cytokines including the transforming growth factor (TGF)-β family, platelet-derived growth factors (PDGF), and epidermal growth factors (EGF). These cytokines stimulate fibroblast proliferation and matrix secretion, and induce leukocyte recruitment. Leukocytes, in turn, reinforce fibroblast activity, fight infection, and increase vascular permeability and ingrowth. They do this acting through the TGF-β family, fibroblast growth factors (FGF), vascular endothelial growth factors (VEGF), and other factors. Prostaglandins and SMAD activation also increase inflammatory cell proliferation and impair matrix breakdown. Increased levels of TGF-β1 and β2 as well as decreased levels of TGF-β3 have been associated with hypertrophic scarring through inflammatory cell stimulation, fibroblast proliferation, adhesion, matrix production, and contraction. Consistent with these observations, anti-inflammatory agents (cytokine inhibitors, corticosteroids, interferon α and β, and methotrexate) have been used with some success to reduce scar formation.

Increased vascular density, extensive microvascular obstruction, and malformed vessels have also been observed in hypertrophic scars. These structural changes may account for the persistent high inflammatory cell density observed in hypertrophic scars. Conversely, persistent inflammation could itself contribute to increased vascularity through positive feedback loops.

Many cells are known to be mechanoresponsive. It has recently become clear that cells in the skin are also able to respond to their mechanical environment. Specifically, cell surface molecules such as the integrin family are activated by mechanical forces, leading to increased fibroblast survival as well as to the remodeling of deposited collagen and fibrin. Keratinocyte proliferation and migration are similarly regulated by mechanical stress. Following tissue injury, mechanotransduction may serve a biological function to signal the presence of a tissue defect. Cells experience the highest levels of mechanical stress on the edge of a monolayer and, in the same way, the wound margin experiences high levels of mechanical stress. These stresses may have evolved to stimulate components of wound healing and initiate repair. Differences in exogenous forces may act to change cellular activation in the wound healing milieu and, when overactivated, lead to hypertrophic scar formation. Skin subjected to high levels of stress (secondary to trauma or joint movement) usually demonstrates robust hypertrophic scar formation.

Methods of improving healing, particularly for amelioration of scarring, are of great interest. The present invention addresses this.

PUBLICATIONS

Gurtner et al., published U.S. Patent Application US 2008/0033334 A1. Wong et al., abstract ASC20110510, entitled "Keratinocyte- And Fibroblast-Specific FAK Signaling Critically Mediate Scar Matrix Remodeling During Supraphysiologic Loading". Wong et al. (2011) Surgical Forum Abstracts 213, No. 3S, entitled "Erasing Langer's lines: Establishing a molecular basis for the fibrotic response to tension".

SUMMARY OF THE INVENTION

Compositions and methods are provided for ameliorating the formation of scars at a wound site, in which an effective dose of an inhibitor of focal adhesion kinase (FAK) activity or expression is brought into contact with the skin at the site of the wound, for a period of time sufficient to reduce scarring, e.g. relative to a wound not treated by the methods of the invention. In the methods of the invention, the FAK inhibitor may be administered locally, often topically e.g. by intradermal injection, microneedle injection, etc or may be comprised in a bandage or other form of wound dressing that is removably secured to a skin surface in proximity to the wound site. The inhibitor may be administered in a formulation that enhances transdermal penetration.

It is shown herein that blockade of FAK is sufficient to prevent mechanical and inflammatory stimuli from activating MCP-1 pathways. In addition to these chemokine-mediated mechanisms, inhibition of FAK may control fibrosis by blocking fibroblast collagen production. Pharmacologic blockade of FAK significantly reduces scar formation in vivo, e.g. by reducing the gross scar area by at least about 25%, at least 50%, at least about 100%, at least about 125%, at least about 150% or more.

Optionally the FAK inhibitor is combined with a device or wound dressing configured to shield the wound from endogenous (i.e., dermal) or exogenous (i.e., physiological) stress, and in some variations, the devices are configured to shield the wound from both endogenous and exogenous stress.

The wound dressing or devices may be removably secured to the skin surface in a variety of ways. For example, the dressing devices may be removably secured to the skin surface with an adhesive, with a skin piercing device, or the like. Suitable adhesives include pressure sensitive adhesives, such as polyacrylate-based, polyisobutylene-based, and silicone-based pressure sensitive adhesives. Suitable skin-piercing devices include microneedles, sutures, anchors, staples, microtines and the like.

Other aspects of the invention include methods for manufacturing a medical device or wound dressing, comprising the step of coating (e.g., spraying, dipping, wrapping, or administering drug through) a medical device or wound dressing with an effective dose of an FAK inhibitor. Additionally, the wound dressing or medical device can be constructed so that the device itself is comprised of materials that inhibit fibrosis.

Other aspects of the invention include wound dressing and medical devices comprising an effective dose of an FAK inhibitor. The inhibitor may be present in such a composition in combination with a polymer. In one embodiment of this aspect, the polymer is biodegradable. In another embodiment of this aspect, the polymer is non-biodegradable. The FAK inhibitor may be sprayed, coated, embedded and the like in such a wound dressing or device, and may be comprised in a gel layer, e.g. for sustained release of the FAK inhibitor.

In another aspect, the present invention provides methods for treating and/or preventing surgical adhesions, comprising contacting tissues at the site with an effective dose of an FAK inhibitor. The surgical adhesions can be the result of, for example, spinal or neurosurgical procedures, of gynecological procedures, of abdominal procedures, of cardiac procedures, of orthopedic procedures, of reconstructive procedures, and cosmetic procedures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF THE SPECIFIC EMBODIMENTS

Figure 1:
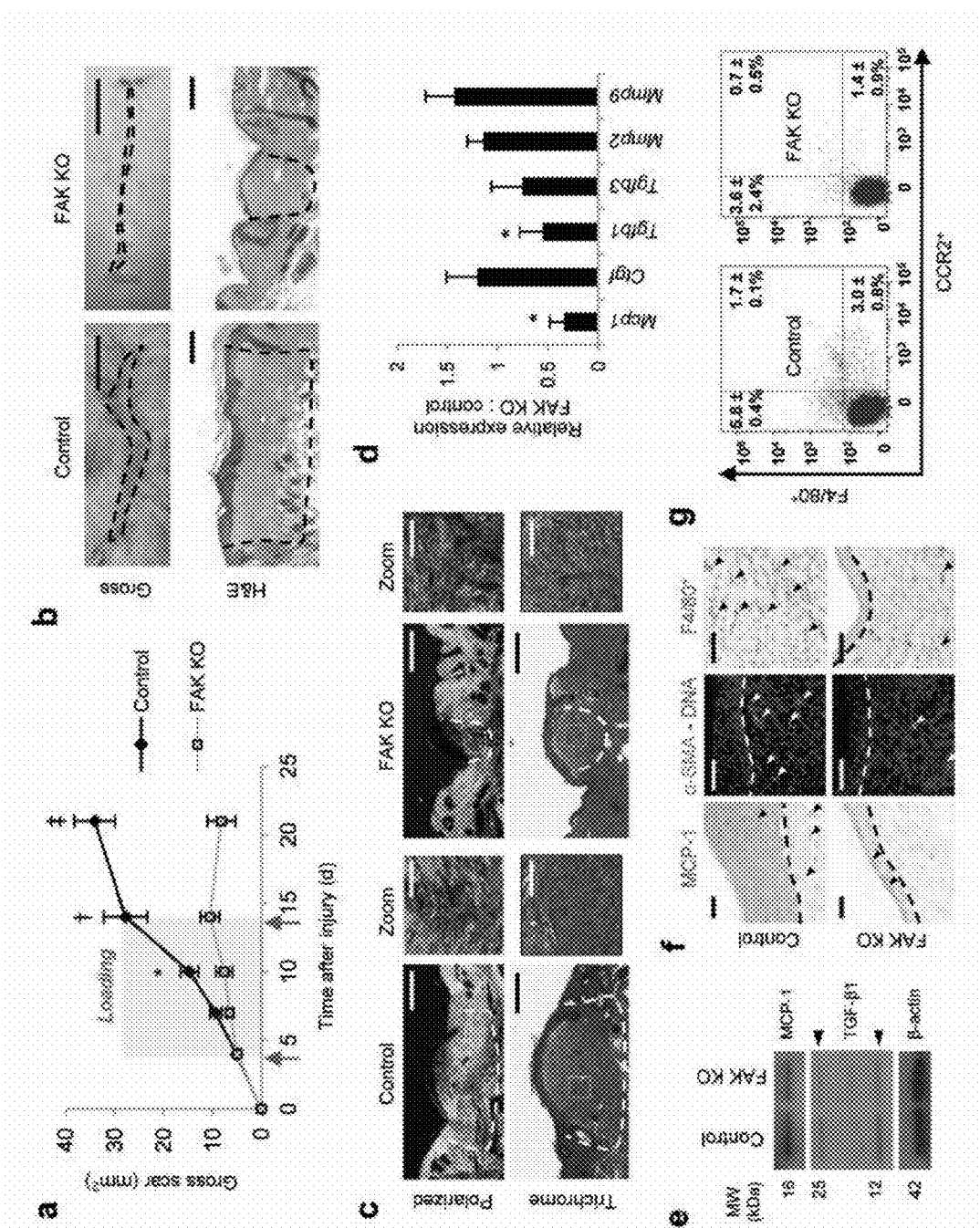
FIG. 1 HTS model. (a) Surface scar formation. n=6. (b) Images of post-injury day ten scars. Scale bar 0.5 cm top; 200 μm bottom. (c) Polarized light and trichrome-stained images. n=6. Scale bar 200 μm; zoom 50 μm. (d) qPCR analysis of wound cytokines. n=9. (e) Scar cytokine densitometry. Arrowheads point to monomer and dimer forms of Tgf-β1. n=3. (f) Immunolocalization of Mcp-1, α-SMA$^+$ cells and F4/80$^+$ macrophages. Scale bar 20 μm left column, 50 μm middle/right columns. n=6. (g) F4/80 and Ccr2 flow cytometry. n=4. Values represent means±s.e.m. *$p<0.05$, †$p<0.01$, ‡$p<0.001$.

Exuberant fibroproliferation is a common complication following injury for reasons that remain poorly understood. It is shown herein that FAK is activated following cutaneous injury and that this process is potentiated by mechanical loading. FAK acts via extracellular-related kinase (ERK) to mechanically trigger the secretion of monocyte chemoattractant protein-1 (MCP-1/CCL2), a potent chemokine linked to human fibrotic disorders. Inhibition of FAK blocks these effects in human cells and significantly reduces scar formation in vivo through attenuated MCP-1 signaling and inflammatory cell recruitment.

Compositions and methods are provided for ameliorating the formation of scars at a wound site, in which an effective dose of an inhibitor of focal adhesion kinase (FAK) activity or expression is brought into contact with the skin at the site of the wound, for a period of time sufficient to reduce scarring, e.g. relative to a wound not treated by the methods of the invention. Aspects of the disclosure provide methods for treating an injury, re-epithelialization of a wound, preventing or reducing scarring during healing of a wound of the skin, wherein an effective dose of an FAK inhibitor is administered to a subject. This includes an injectable formulation administered over a period of time sufficient to obtain a therapeutic effect. In one embodiment, the subject is a human subject. In other embodiments, the injury is a cut, which can be an incision of the epidermis, or a wound, which may be open or closed. Examples of open wounds include, but are not limited to, an incision, a laceration, an abrasion, a puncture wound, a penetration wound, a gunshot wound, and/or a stabbing wound.

The mechanical environment of an injury can be an important factor in tissue response to that injury. The mechanical environment includes exogenous stress (i.e., physiological stress which includes stress transferred to the wound via muscle action or physical body movement) and endogenous stress (i.e., dermal stress originating from the physical properties of the skin itself, including stress induced at the wound site due to swelling or contraction of the skin). The skin includes the outer stratum corneum, the epidermis and dermis. The devices, bandages, kits and methods described herein optionally control or regulate the mechanical environment of a wound to ameliorate scar and/or keloid formation, as described in co-pending application US 2008/0033334 A1, herein specifically incorporated by reference. Unloading of exogenous and/or endogenous stress in the vicinity of the wound can ameliorate the formation of scars, hypertrophic scars, or keloids.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

DEFINITIONS

Focal adhesion kinase (FAK), also known as cytoplasmic protein-tyrosine kinase (PTK2) is a cytosolic protein tyrosine kinase concentrated in the focal adhesions that form among cells attaching to extracellular matrix constituents (see Andre et al. (1993) Biochem. Biophys. Res. Commun. 190: 140-147). FAK is a highly conserved, non-receptor tyrosine kinase of 125 kD, which is recruited as a participant in focal adhesion dynamics between cells, and has a role in motility and cell survival. FAK is phosphorylated in response to integrin engagement, growth factor stimulation, and the action of mitogenic neuropeptides. A carboxy-terminal region of one hundred and fifty-nine amino acids, the focal adhesion targeting domain (FAT), has been shown to be responsible for targeting FAK to focal adhesions. Paxillin, a focal adhesion adaptor protein binds to FAK at a carboxy-terminal domain that overlaps the FAT domain. Between the amino and the carboxy regions lies the catalytic domain. Phosphorylation of the activation loop within this kinase domain is important for the kinase activity of FAK.

Inhibitors of FAK. A number of FAK inhibitors are known and used in the art. Non-limiting examples include PF-573, 228; PF-562,271; FAK Inhibitor 14, bortezomib; (for example see Cabrita et al. (2011) Mol. Oncol. 5(6):517-26; Ko et al. (2010) Anticancer Agents Med Chem 10(10):747-52; Li and Hua (2008) Adv. Cancer Res 101:45-61; WO 2008/115369 which describes inhibitors of FAK as derivatives of a 5-substituted 2,4-diaminopyridine; WO 2003/035621 which describes protein kinase inhibitors; and U.S. Pat. No. 7,067,522 which describes 2,4,DI (hetero-) arylamino (-oxy)-5-substituted pyrimidines as inhibitors of FAK, each of which is herein individually and specifically incorporated by reference.) Inhibitors of interest include small molecule inhibitors, as well as biologicals such as antibodies, RNAi, antisense, peptide inhibitors and peptidomimetics, and the like.

Antimicrobial agents. The formulations and wound dressings may further comprise antimicrobial agents. Agents of interest include a wide variety of antibiotics, as known in the art. Classes of antibiotics include penicillins, e.g. penicillin G, penicillin V, methicillin, oxacillin, carbenicillin, nafcillin, ampicillin, etc.; penicillins in combination with β lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc. Antiviral agents, e.g. acyclovir, gancyclovir, etc. may also be included.

Wound dressing or bandages. Bandages to ameliorate the formation of a scar and/or keloid at a wound site are provided. In general, the bandages are configured to be removably secured to a skin surface, may include one or more active agents. The bandages may have any suitable shape or size. At least a portion of the bandage may be made from a transparent material, and the bandages may or may not be occlusive.

Bandages may also include a hydrogel films for use as a wound dressing, or artificial skin, by providing an improved substrate that minimizes scarring. An effective bioactive wound dressing can facilitate the repair of wounds that may require restoration of both the epidermis and dermis. An hydrogel thin film is placed onto, and accepted by, the debrided wound of the recipient and provide a means for the permanent re-establishment of the dermal and epidermal components of skin.

Additional criteria for biologically active wound dressings include: rapid adherence to the wound soon after placement; proper vapor transmission to control evaporative fluid loss from the wound and to avoid the collection of exudate between the wound and the dressing material. Skin substitutes should act as barrier to microorganisms, limit the growth of microorganisms already present in the wound, be flexible, durable and resistant to tearing. The substitute should exhibit tissue compatibility, that is, it should not provoke inflammation or foreign body reaction in the wound which may lead to the formation of granulation tissue. An inner surface structure of an hydrogel thin film is provided that permits ingrowth of fibro-vascular tissue. An outer surface structure may be provided to minimize fluid transmission and promote epithelialization.

Typical bioabsorbable materials for use in the fabrication of porous wound dressings, skin substitutes and the like, include synthetic bioabsorbable polymers such as polylactic acid or polyglycolic acid, and also, biopolymers such as the structural proteins and polysaccharides.

FAK inhibitors may be formulated as pharmaceuticals to be used in the methods of the disclosure. Any composition or compound that can inhibits a biological response associated FAK activation, (e.g., small molecule FAK inhibitor, inhibitor of FAK gene expression, etc.) can be used as a pharmaceutical in the disclosure. General details on techniques for formulation and administration are well described in the scientific literature (see Remington's Pharmaceutical Sciences, Maack Publishing Co. Easton Pa.). Pharmaceutical formulations containing pharmaceutically active FAK inhibitor can be prepared according to any method known in the art for the manufacture of pharmaceuticals. The formulations containing pharmaceutically active FAK inhibitor used in the methods of the disclosure can be formulated for administration in any conventionally acceptable way including, but not limited to, topically, intravenously, systemically, subcutaneously. intramuscularly, sublingually. and via inhalation or injection, irrigation or an osmotic pump. Topical administration and intradermal injection are of particular interest.

For example, a FAK inhibitor may be applied either as an irrigation fluid to an open wound, as a topical application to a wound that has covered, and/or systemically during any stage of wound repair. A formulation could be injected near the wound site or scar, or may be a cream that would be rubbed in to a wound site or scar to lengthen residence time and penetration. Treatment via irrigation involves, for example, slowly dripping 0.5 ml of a FAK inhibitor solution in sodium acetate onto the wound site. In other embodiments, the ranges for dripping FAK inhibitor solutions onto wounds may range from about 0.5 ml to about 5.0 ml or higher onto a wound site. Wounds are irrigated, for example, once daily for seven days following the lesion. In another embodiment, wounds are irrigated, for example, twice or more often per day for about seven days following the lesion. In yet other embodiments, wounds are irrigated weekly or monthly for a longer or shorter duration following the lesion. Dosages for purposes of FAK inhibitor administration may be adjusted according to the severity of the lesion and condition of the patient.

Topical compositions may comprise an effective dose of an FAK inhibitor according to the invention, and a dermatologically acceptable vehicle. The dose present in a topical composition may be at least about 0.1 µg, at least about 1 µg, at least about 10 µg, at least about 100 µg, at least about 1 mg, at least about 10 mg, at least about 100 mg, or more. The inhibitor may be available as an application unit and applied directly on to the skin in the form of a gel, cream, spray or ointment. A typical dose for a topical formulation is from about 1 µl to about 100 µl to about 1 ml, to about 10 ml, applied in a lotion, cream, gel, etc. to the affected skin. In use, a small quantity of the composition is applied to exposed areas of the skin, from a suitable container or applicator and, if necessary, it is then spread over and/or rubbed into the skin using the hand or fingers or a suitable device.

In some embodiments, the topical formulation comprises skin penetration enhancers. Such enhancers reversibly decrease skin barrier resistance, and include without limitation, sulphoxides (such as dimethylsulphoxide, DMSO), azones (e.g. laurocapram), pyrrolidones (for example 2-pyrrolidone, 2P), alcohols and alkanols (ethanol, or decanol), glycols (for example propylene glycol, PG, a common excipient in topically applied dosage forms), surfactants (also common in dosage forms) and terpenes.

Dimethyl sulfoxide (DMSO) is of particular interest as a penetration enhancer. It is a powerful aprotic solvent that hydrogen bonds with itself rather than with water; it is colorless, odorless and is hygroscopic and is often used in many areas of pharmaceutical sciences as a solvent (Williams and Barry, 2004, Adv Drug Deliv Rev, 56, 603-18). DMSO as a as a skin penetration agent is used in concentrations varying from 5-99%, gels containing 10% DMSO have shown best skin permeation (Baboota, Shakeel and Kohli, 2006, Methods Find Exp Clin Pharmacol, 28, 109-14). Formulations of interest may comprise at least about 5% DMSO, at least about 10% DMSO, at least about 25% DMSO, at least about 35% DMSO, at least about 50% DMSO, at least about 60% DMSO, at least about 75% DMSO, at least about 85% DMSO, at least about 95% DMSO, at least about 99% DMSO, usually calculated as volume/volume.

In yet another preferred embodiment, FAK inhibitor can be delivered to the wound site by intravenous or intradermal injection, wherein the formulations contain pharmaceutically active FAK inhibitor in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a nontoxic parenterally-acceptable diluent or solvent. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic monoglycerides or diglycerides. In addition, fatty acids such as oleic acid can likewise be used in the preparation of injectables.

Aqueous suspensions of the disclosure contain FAK inhibitor in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e g, lecithin), a condensation product of an alkylene oxide with a fatty acid (e g, polyoxyethylene stearate), a condensation product of ethylene oxide with a long chain aliphatic alcohol (e g, heptadecaethylene oxycetanol). a condensation product of ethylene oxide with a partial ester derived from a fatty acid and a hexitol (e g, polyoxyethylene sorbitol mono-oleate), or a condensation product of ethylene oxide with a partial ester derived from fatty acid and a hexitol anhydride (e g, polyoxyethylene sorbitan monooleate). The aqueous suspension can also contain one or more preservatives, one or more coloring agents, one or more flavoring agents and one or more sweetening agents, such as sucrose, aspartame or saccharin. Formulations can be adjusted for osmolarity.

Dispersible powders and granules of the disclosure suitable for preparation of an aqueous suspension by the addition of water can be formulated from FAK inhibitor in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, can also be present.

The pharmaceutical formulations of the disclosure can also be in the form of oil-in-water emulsions. The oily phase can be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate. and condensation products of these partial esters with ethylene oxide, such as polyoxyethylene sorbitan mono-oleate. The emulsion can also contain sweetening and flavoring agents. Syrups and elixirs can be formulated with sweetening agents, such as glycerol, sorbitol or sucrose. Such formulations can also contain a demulcent, a preservative, a flavoring or a coloring agent.

Additional active agents that may be desirable for use with the bandages and devices described here include, but are not limited to growth factors, enzymes such as elastase to degrade the extra cellular matrix, proteases such as aspartate, serine, and metalloproteases that are capable of digesting and remodeling tissue, inhibitors of enzymes such as tissue inhibitors of metalloproteases, antibiotics, antifungals, vitamin E, and combinations thereof. In some variations, delivery of active agents can be controlled by time-release, e.g., by encapsulating or embedding the active agents in a time-release formulation, such as a drug delivery polymer or depot.

The term "wound" generally refers to both open and closed wounds, as defined below. A wound can be further classified as an acute or chronic wound. An acute wound is one that does not have an underlying healing defect, and usually occurs secondarily to surgery or trauma in a healthy individual, healing quickly and completely. In contrast, a chronic wound is one that has a loss in tissue integrity, produced by insult or injury that is of extended duration or frequent recurrence. As used herein, the term "skin wound" refers to a break in the skin.

The term "open wound" is usually classified according to the object that caused the wound. This includes incisions, lacerations, abrasions, puncture wounds, penetration wounds, gunshot wounds and the like. Incisions or incised wounds may be caused by a clean, sharp-edged object such as a knife, a razor, or a glass splinter. Incisions involving only the epidermis can be classified as cuts. Lacerations are irregular wounds caused by a blunt impact to soft tissue that lies over hard tissue (such as laceration of the skin covering the skull) or tearing of skin and other tissues (such as caused by childbirth). Lacerations may show bridging, as connective tissue or blood vessels are flattened against the underlying hard surface. Abrasions (grazes) are superficial wounds in which the topmost layer of the skin (the epidermis) is scraped off, and are often caused by a sliding fall onto a rough surface. Puncture wounds may be caused by an object puncturing the skin, such as a nail or needle. Penetration wounds may be caused by an object such as a knife entering the body. Gunshot wounds are caused by a bullet or similar projectile driving into or through the body. As such, there may be two wounds, one at the site of entry and one at the site of exit, which is generally known as a through-and-through.

The term "closed wound" refers to contusions, more commonly known as bruises, caused by blunt force trauma that damages tissue under the skin; hematomas, also called blood tumors, caused by damage to a blood vessel that in turn causes blood to collect under the skin; and crushing injuries, which may be caused by a great or extreme amount of force applied over a long period of time.

The term "scar" refers to an abnormal morphological structure resulting from a previous injury or wound (e.g., an incision, excision or trauma). Scars are composed of a connective tissue which is predominately a matrix of collagen types 1 and 3 and fibronectin. A scar may consist of collagen fibers in an abnormal organization (as seen in normal scars of the skin) or may be an abnormal accumulation of connective tissue (as seen in scars of the central nervous system or pathological scarring of the skin). The types of scars include, but are not limited to, atrophic, hypertrophic and keloidal scars, as well as scar contractures. Atrophic scars are flat and depressed below the surrounding skin as a valley or hole. Hypertrophic scars are elevated scars that remain within the boundaries of the original lesion, and often contain excessive collagen arranged in an abnormal pattern. Keloidal scars are elevated scars that spread beyond the margins of the original wound and invade the surrounding normal skin in a way that is site specific, and often contain whorls of collagen arranged in an abnormal fashion. Scar contractures are scars that cross joints or skin creases at right angles, and are prone to developing shortening or contracture. Scar contractures occur when the scar is not fully matured, often tend to be hypertrophic, and are typically disabling and dysfunctional.

A variety of conditions may cause scarring, including surgical wounds, burns, cuts, gunshot, etc. Scars commonly form as a result of facial plastic surgery, which includes, but is not limited to, rhytidectomy, blepharoplasty, rhinoplasty, otoplasty, mentoplasty. face lift, fore head lift, brow lift, facial scar revision, facial scar removal, laser surgery, skin resurfacing, wrinkle treatment, plasma skin regeneration, facial fat grafting, skin tightening, tattoo removal and hair replacement. Thus, this disclosure is advantageous to patients who undergo facial plastic surgery, particularly to aid with scarring and bruising, by speeding up wound healing and reducing scar formation. Scars also commonly form as a result of full-body plastic surgery, which includes, but is not limited to abdominoplasty, breast reduction, breast enhancement, body lift procedures, spider vein treatment, stretch mark treatment, liposuction, excess skin removal surgery, cellulite reduction treatment, body contouring, body resurfacing and body implants.

"Administering" refers to giving or applying to a subject a pharmaceutical remedy or formulation via a specific route, including but not limited to, topically, intradermal injection, intravenously, systemically, subcutaneously, intramuscularly, sublingually, and via inhalation or injection, irrigation or an osmotic pump.

Devices and Methods

Methods for ameliorating the formation of scars and/or keloids are provided, comprising the step of contacting a wound with an effective dose of an FAK inhibitor for a period of time sufficient to reduce scarring. As described above, various methods find use, e.g. bandages or wound dressings comprising an FAK inhibitor, lotions, gels, and other topical formulations, injection or microneedle injection of a pharmaceutical formulation of an FAK inhibitor at the site of a wound, and the like. The dose of inhibitor will depend on the activity of the compound, the manner of dosing, and the like as known in the art. Empirical methods may be utilized to determine an effective dose, e.g. using in vivo or in vitro models as set forth in the examples. In some embodiments an effective dose may be at least about least about 0.1 µg, at least about 1 µg, at least about 10 µg, at least about 100 µg, at least about 1 mg, at least about 10 mg, at least about 100 mg per unit dose.

The agent may be maintained in contact with the wound, e.g. in a sustained release wound dressing, or may be administered once or for a period of time, e.g. daily, semi-daily, every two days, every three days, every four days, etc., usually for at least about 1 day, at least about 2 days, at least about 3 days, at least about 1 week, at least about 10 days, at least about 2 weeks, at least about 3 weeks, or more. For example, in some variations, it is desirable to apply the devices to the wound site from about one to about three days following injury, i.e., during an initial period such as the early part of the proliferative phase. It should be understood that the devices may or may not be applied to a wound site where the wound has already initially been closed (e.g., by suturing, adhesives, bandages or the like). Similarly, the devices may be applied to a fresh wound caused by a scar removal procedure. In some instances, the device will be applied up to seven days following injury, i.e., later in the proliferative phase. For example, swelling and wound exudates may indicate that the devices be applied later than three days following injury. In some applications, a first bandage can be applied within an initial period following injury, e.g., within the first three days, and then removed, and a second bandage can be applied thereafter. The second bandage can be adapted to changes in the skin and tissue surrounding the wound that can occur after the initial period, e.g., decreased swelling and exudates.

The subject methods find use in any application in which the treatment of a wound of a subject is desired. Generally, such subjects are "mammals" or "mammalian", where these terms are used broadly to describe organisms which are within the class mammalia, including the order carnivore (e.g., dogs and cats), rodentia (e.g., mice, guinea pigs, and rats), and primates (e.g., humans, chimpanzees, and monkeys). In many embodiments, the subject is a human.

Accordingly, the subject methods may be used to treat a wide variety of open- and closed-skin wounds such that the subject methods may be used to treat wounds that have resulted from a variety of causes, e.g., as a result of a condition such as a disease state, a physical injury such as a fall, scrape, stab wound, gun shot, surgical wound, infection, etc., wartime injuries such as bombs, bullets, shrapnel. Likewise, the subject methods may treat wounds of various dimensions. For example, the subject methods may be employed to with both deep tissue wounds and shallow or superficial wounds, where certain wounds may have depths that reach the muscle. Wounds may be confined to the epidermis such that they do not penetrate into the dermal layer, may be as deep as the dermis or deeper, e.g., may penetrate to or through the dermis and even to or through the subcutaneous tissue layer or deeper, e.g., may penetrate through or to the muscle layer or further. For example, the subject methods may be used to debride wounds that having a depth that ranges from about 0.005 mm to about 2.35 mm, e.g., from about 0.007 mm to about 2.3 mm, e.g., from about 0.01 mm to about 2 mm.

Types of wounds that may be treated with the subject invention include, but are not limited to, ulcers, including pressure ulcers, diabetic ulcers (e.g., diabetic foot ulcers), venous ulcers, lower leg ulcer, etc.; burns (first, second and third degree burns) including scalds, chemical burns, thermal burns such as flame burns and flash burns, ultraviolet burns, contact burns, radiation burns, electrical burns, etc.; bone infections (osteomyelitis); gangrene; skin tears or lacerations, such as made by knives, etc.; abrasions; punctures such as made by nails, needles, wire, and bullets, etc.; incisions such as made by knives, nails, sharp glass, razors, etc.; avuls; amputations; post-operative infections; surgical wounds; brown recluse spider wounds; failing or compromised skin/muscle grafts or flaps; bites; slash wounds, i.e., a wound where the length is greater than the depth; bruises; and the like, or a combination of one or more of the above.

Devices are also described here for ameliorating the formation of scars and/or keloids at a wound site. The scars may be any type of scar, e.g., a normal scar, a hypertrophic scar, etc. In general, the devices are configured to be removably secured to a skin surface near a wound. The devices of the invention comprise an effective dose of an FAK inhibitor. A diverse array of additional active agents or ingredients may be present in the compositions. Depending on the nature of the agent, the amount of active agent present in the composition may ranges from about 0.2 to 10%, e.g., from about 0.2 to 5%, e.g., from about 0.5 to 5%. The pH typically is one that lies in a physiologically acceptable range, where the pH typically ranges from about 3.0 to 8.0 and more typically ranges from about 4.0 to 7.0.

A wound dressing comprising an effective dose of an FAK inhibitor, e.g. embedded in a hydrogel or other polymer patch, and may be attached or adhered to a substrate, e.g. a breathable protective layer, or other protective film. Alternatively the dressing may be separately configured from a protective dressing. The support is generally made of a flexible material which is capable of fitting in the movement of the human body and includes, for example, various non-woven fabrics, woven fabrics, spandex, flannel, or a laminate of these materials with polyethylene film, polyethylene glycol terephthalate film, polyvinyl chloride film, ethylene-vinyl acetate copolymer film, polyurethane film, and the like. By "flexible" it is meant that the support may be substantially bent or folded without breaking, tearing, ripping, etc. The support may be porous or non-porous, but is typically non-porous or impermeable to the hydrogel composition, active agent if employed and fluids, e.g., any fluids exuded from the wound site.

The length and width dimensions of the support are typically substantially commensurate, including exactly commensurate, with the length and width dimensions of the patch composition with which it is associated. The support layer typically may have a thickness that ranges from about 10 µm to about 1000 µm, but may be less than about 10 µm and/or greater than 1000 µm in certain embodiments.

In addition to the patch and the optional support layer, the dressing may also include a release film on the surface of the hydrogel composition layer opposite a backing that provides for protection of the patch layer from the environment. The release film may be any convenient material, where representative release films include polyesters, such as PET or PP, and the like.

The shape of the dressing may vary, where representative shapes include square, rectangle, oval, circle, triangular, etc. The size of the dressing may also vary, where in many embodiments the size ranges from about 1 $cm^2$ or less to about 1000 $cm^2$ or more, e.g., in certain embodiments ranges from about 10 to about 300 $cm^2$, e.g., from about 20 to about 200 $cm^2$, e.g., about 130 $cm^2$ to about 150 $cm^2$. In certain embodiments, the surface area is sufficient to cover a substantial portion or even the entire truck or even a substantial portion of the entire body or even the entire body of a subject. Accordingly, the surface area may range from about 1000 $cm^2$ to about 5000 $cm^2$ or more. It should be noted that the above manufacturing protocol is merely representative. Any convenient protocol that is capable of producing the subject hydrogel patch compositions, as described above, may be employed.

The devices and bandages described herein may have any suitable shape. For example, the devices or bandages may be rectangular, square, circular, oval, toroidal, or segments or combinations thereof. In many variations, the devices will be flexible and planar to allow conformal placement against skin. Of course, the devices and bandages may also be of any suitable size, to deal with a variety of wounds. In some variations, the devices and bandages may be cut immediately prior to use from a roll or sheet of bandage to ensure appropriate coverage of the wound site. Devices and bandages can extend out to about 20 cm (about 8 inches) from the wound in some instances, and in other instances the devices or bandages can extend about 2, 4, 6, 8, 10, 12, 14, 16, or 18 cm from the wound, where "about" qualifies each of the distances. In still other variations, the bandages can extend about 22 cm, about 24 cm, about 26 cm, or even more, from the wound. In some variations, the devices are made from a polymer, for example, a shape memory polymer. Any suitable shape memory polymer may be used, e.g., styrene-based, epoxy-based, or acrylate-based shape memory polymers.

Kits for ameliorating the formation of scars and/or keloids are also described here. In general, the kits comprise in packaged combination a unit dosage of an effective amount of an FAK inhibitor, which may be provided as a lyophilized composition suitable for reconstitution, an injectable solution, a sealed bandage, and the like. Multiple doses in a kit may be designed to be applied in parallel. For example, some kits may include one formulation to be applied during an initial period such as the early part of the proliferative phase of wound healing, e.g., up to three days after injury, and then removed and a second formulation to be applied thereafter. Some kits may contain at least one wound dressing, or at least one wound cleanser, or other components desirable or suitable for wound healing applications. The kits may also comprise instructions for using the devices and/or other components contained therein.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention.

EXPERIMENTAL

Example 1

Focal Adhesion Kinase Links Mechanical Force to Skin Fibrosis Via Inflammatory Signaling Exuberant fibroproliferation is a common complication following injury for reasons that remain poorly understood. One important component of wound repair that is often overlooked is mechanical force, which regulates cell-matrix interactions through intracellular focal adhesion components including focal adhesion kinase (FAK). Here we report that FAK is activated following cutaneous injury and that this process is potentiated by mechanical loading. Fibroblast-specific FAK knockout (KO) mice exhibit significantly less inflammation and fibrosis in a model of hypertrophic scar (HTS) formation. We demonstrate that FAK acts via extracellular-related kinase (ERK) to mechanically trigger the secretion of monocyte chemoattractant protein-1 (MCP-1/CCL2), a potent chemokine linked to human fibrotic disorders. Similarly, MCP-1 KO mice form minimal scar, indicating that inflammatory chemokine pathways are a major mechanism by which FAK mechanotransduction induces fibrosis. Small molecule inhibition of FAK blocks these effects in human cells and significantly reduces scar formation in vivo through attenuated MCP-1 signaling and inflammatory cell recruitment. These findings collectively indicate that physical force regulates fibrosis via inflammatory FAK/

ERK/MCP-1 pathways and that molecular strategies targeting FAK can effectively uncouple mechanical force from pathologic scar formation.

Traditional cytokine-based paradigms for fibrosis largely overlook the importance of cell-matrix interactions and physical cues in disease pathogenesis. However, clinicians and anatomists have suspected for centuries that mechanical forces influence the fibrotic response to cutaneous injury with numerous studies suggesting the importance of reducing wound tension to decrease scar formation. Most recently, our group demonstrated that mechanical offloading of incisions can significantly decrease HTS formation in humans, further underscoring the importance of the mechanical environment in cutaneous pathology. Despite these longstanding clinical observations, the molecular pathways linking physical force with fibrosis remain unknown.

We previously demonstrated that mechanical force induced HTS-like fibrosis in a murine model of cutaneous scarring. To elucidate candidate pathways driving early scar formation, we performed genomewide microarray analysis on wildtype murine scars that had been subjected to human-like levels of skin tension (0.15-0.27 N mm$^2$) between days 4 to 14 post-injury. Construction of transcriptome networks around mechanically regulated genes implicated a central role for FAK as a transducer of both inflammatory and physical signals. To test this concept, we examined whether FAK is activated following either incisional injury or loading of unwounded skin. Notably, we found that cutaneous injury activated FAK and that mechanical force significantly potentiated this effect, leading us to hypothesize that FAK is a key mediator of both inflammation and fibrosis.

Although current mechanotransduction research implicates a role for both integrin-matrix interactions and FAK in the cellular response to force, the importance of these mechanisms on a complex tissue/organ level remains unclear. Previous studies utilizing keratinocyte-specific FAK KO mice reported no wound healing phenotype, suggesting that dermal FAK signaling may be more important for cutaneous repair. Accordingly, we focused on the role of FAK specifically in dermal fibroblasts, the end effector for fibrosis and scar formation. To generate adult dermal fibroblast-restricted FAK KO mice, floxed FAK mice (FAK$^{loxP/loxP}$)[16] were crossed with tamoxifen-inducible Col1α2-Cre mice (Col1α2-Cre$^{+/-}$)[17]. FAK KO progeny (FAK$^{loxP/loxP}$ Col1α2-Cre$^{+/-}$) were viable, fertile, produced at expected Mendelian ratios and exhibited no overt pathologic phenotype.

We then applied the HTS model to FAK KO mice and although normal incisional healing was not impaired, scar formation and matrix density were markedly diminished (FIG. 1a-c). Dermal area and cellularity were decreased by 69% (p=0.002) and 48% (p<0.001), respectively, at post-injury day ten. These effects were associated with impaired proliferation (Ki67 index: 5.5±1.4 FAK KO vs. 13.0±1.7, p<0.001) but apoptosis was unchanged (% apoptotic cells: 6.2±1.1 FAK KO vs. 3.6±0.6, p=0.07), consistent with our recent report suggesting that activation of survival pathways is not a primary factor in scar formation. In vitro motility and contraction assays demonstrated aberrant matrix mechanosensing in FAK KO fibroblasts, suggesting that FAK is necessary to transmit mechanotransduction cues that induce fibrosis.

Because inflammatory mechanisms are strongly implicated in fibrosis, we examined whether FAK modulates cytokine/chemokine signaling, as suggested by our microarray analysis. Consistent with traditional paradigms for fibrosis, transcriptional and protein levels of transforming growth factor-β1 (Tgf-β1) were significantly decreased in FAK KO scars (densitometry 0.7±0.1 vs. 1.4±0.2, p<0.05) (FIG. 1d-e). Notably, levels of Mcp-1, a chemokine highly associated with inflammatory cell recruitment and fibrotic skin diseases, were also attenuated in FAK KO wounds (densitometry 0.4±0.05 vs. 0.6±0.07, p<0.05) (FIG. 1d-e), implicating a key role for MCP-1 in scar mechanotransduction. FAK KO scars exhibited decreased numbers of α-SMA+ myofibroblasts (cells/hpf: 1.6±0.4 vs. 5.8±0.5, p=0.003) and F4/80+ macrophages (cells/hpf: 3.0±0.9 vs. 7.6±0.8, p=0.03) (FIG. 1f), cell populations extensively linked to MCP-1. In addition, overall wound expression of Ccr2 (the surface receptor for MCP-1) was reduced with deletion of FAK (FIG. 1g), indicating a defect in MCP-1-mediated cell trafficking.

Figure 2:
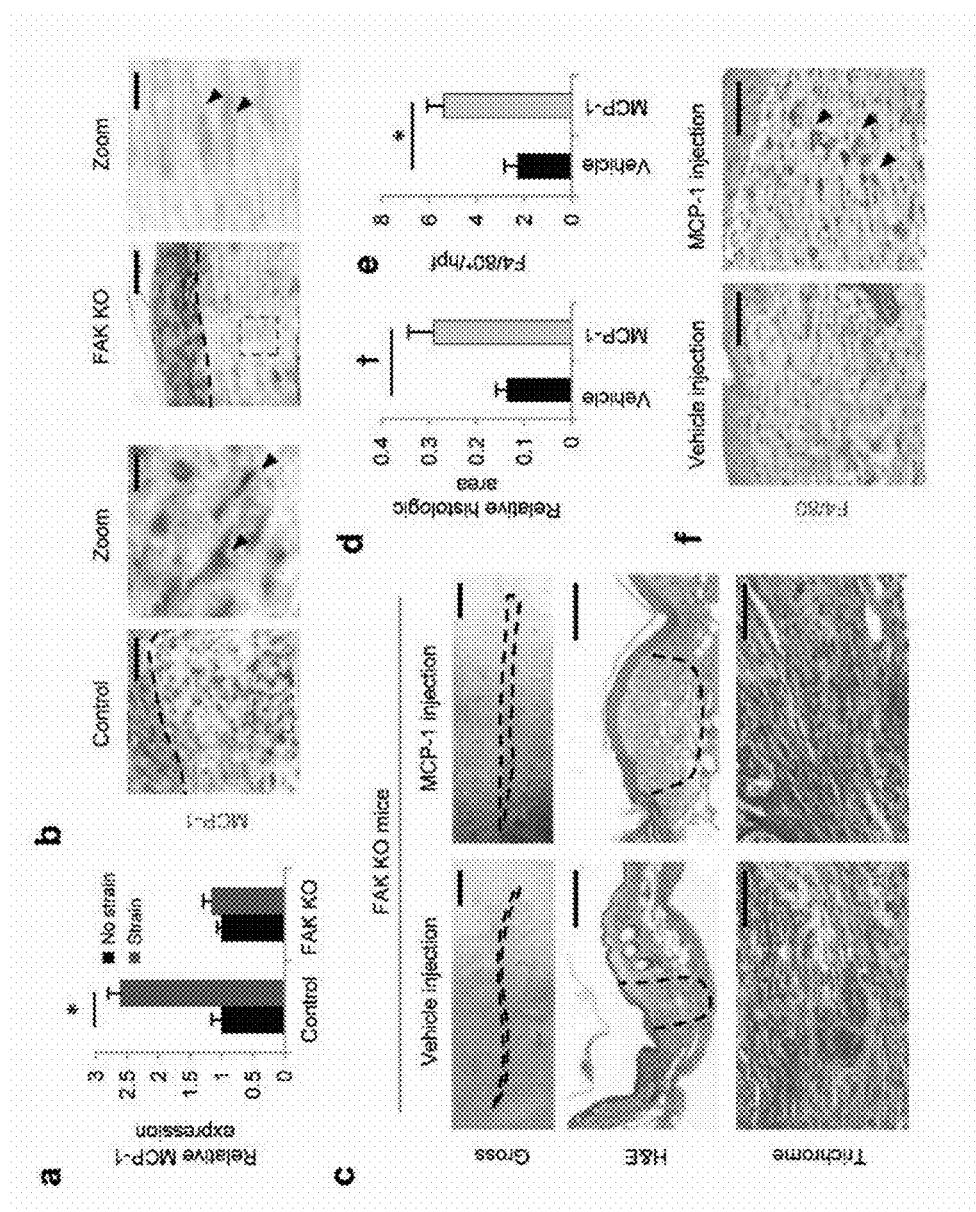
FIG. 2 Fibroblast-specific MCP-1 pathways. (a) Mcp-1 transcription in strained fibroblasts. n=6. (b) Mcp-1 in situ hybridization at day ten (Mcp-1 transcripts stained purple). Arrowheads point to spindle-shaped fibroblasts in high power field (dashed red box). Dashed black line indicates basement membrane. Scale bar 10 μm in zoom. (c) Analysis of fibrosis following intradermal MCP-1 injection. Dashed line outlines scar. Scale bar 0.25 cm top row; 200 μm middle row. (d) Scar area at day ten. n=6. (e) Quantification and (f) images of macrophages in FAK KO scars treated with vehicle or MCP-1. Arrowheads point to macrophages. Values represent means±s.e.m. Scale bar 50 μm unless otherwise noted. *$p<0.001$, †$p<0.05$.

To clarify the importance of fibroblast-specific secretion of MCP-1, FAK KO fibroblasts were subjected to mechanical strain and demonstrated diminished expression of Mcp-1 (FIG. 2a). In situ hybridization studies confirmed markedly decreased levels of fibroblast Mcp-1 transcripts in vivo (FIG. 2b). Finally, intradermal administration of Mcp-1 restored the fibrotic phenotype in FAK-deficient wounds (FIG. 2c-f), confirming the importance of fibroblast secretion of MCP-1 during scar formation. We then applied our HTS model to global MCP-1 KO mice, which demonstrated a 70% reduction in HTS formation relative to wildtype control scars (at post-injury day ten, p=0.001). These MCP-1 KO scars also exhibited significantly reduced recruitment of macrophages (F4/80+cells/hpf: 5.3±0.6 vs. 0.3±0.2, p<0.001), key regulators of matrix remodeling. Together, these findings indicate that MCP-1-dependent inflammatory pathways play a major role in scar mechanotransduction.

To fully elucidate the intracellular signaling events connecting FAK with MCP-1 secretion, we analyzed known downstream mediators of FAK, including Akt and the mitogen-activated protein kinases (MAPK): ERK, p38 and JNK. Only ERK was both activated by mechanical stimuli and differentially regulated by FAK, corroborating previous in vitro findings implicating ERK as a key target of FAK mechanotransduction. Together, these data underscore the importance of FAK-ERK pathways in wound mechanosensing and indicate that MCP-1 may be a key effector of FAK/ERK-mediated fibrosis.

Figure 3:
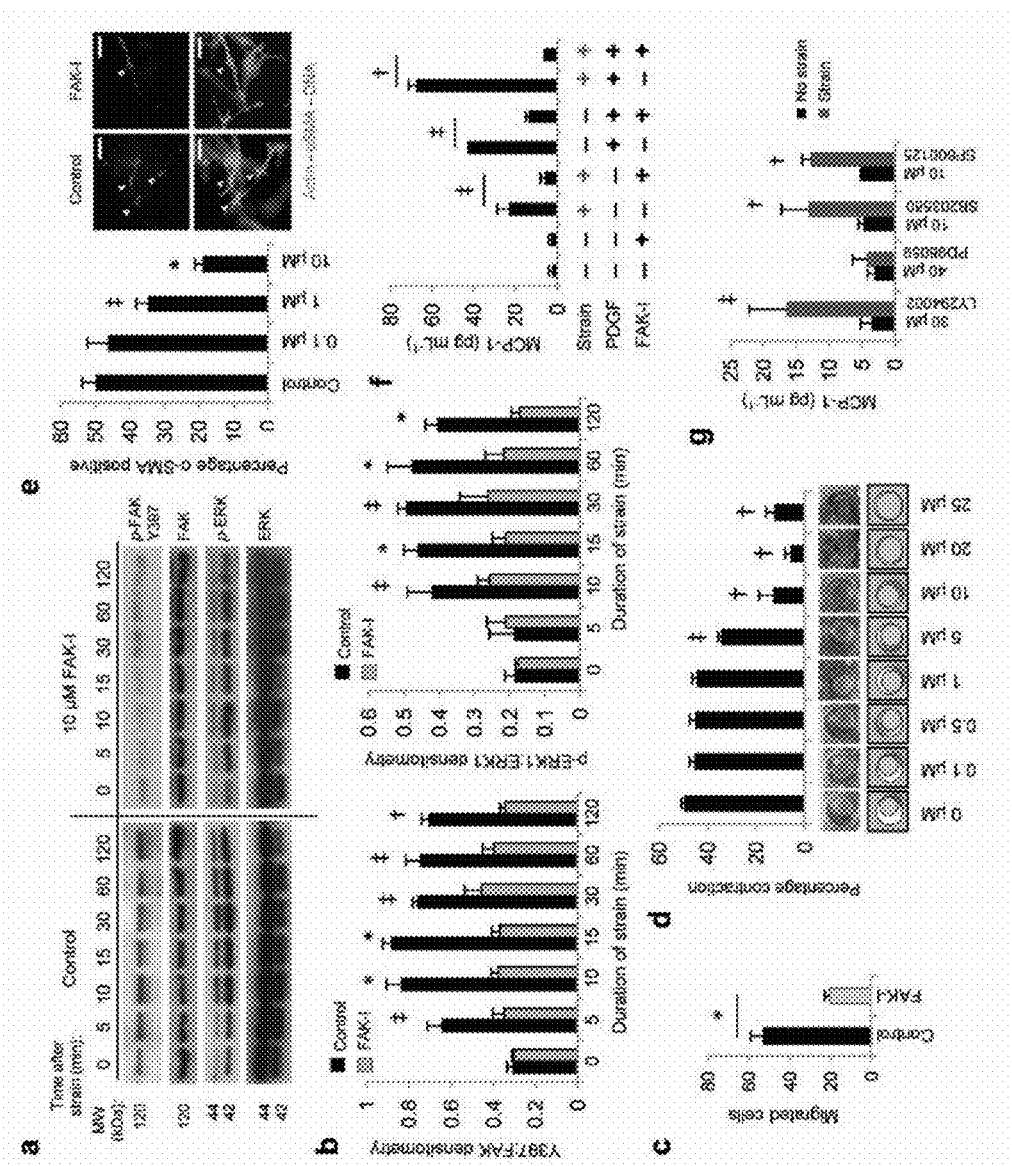
FIG. 3 FAK-mediated mechanoresponsive pathways in human fibroblasts. (a-b) Representative immunoblots and quantification of static strain-induced FAK and ERK activation. n=3. (c) Fibroblast motility in scratch migration assay. n=6. (d) Fibroblast contraction and (e) α-SMA expression (arrowheads) in 3D-collagen lattices. n=3. Scale bar 50 μm. (f) Synergistic (strain+10 ng mL$^{-1}$ PGDF) induction of MCP-1 secretion. n=4 (g) Strain-induced MCP-1 secretion with small molecule inhibition of FAK (PF573228), Akt (LY294002), ERK (PD98059), p38 (SB203580) or JNK (SP600125). n=4. Values represent means±s.e.m.; *$p<0.001$, †$p<0.01$, ‡$p<0.05$.

To substantiate the importance of these findings in human tissues, we examined FAK pathways in vitro in human fibroblasts. Following the application of strain, FAK was activated within five minutes and sustained during the static strain period (FIG. 3a-b). ERK was phosphorylated after ten minutes and its activation was critically dependent on FAK, thus recapitulating the FAK-ERK mechanotransduction axis observed in vivo. Small molecule inhibition of FAK (PF573228) was used to investigate mechanically-regulated fibroblast function during wound repair. We found that PF573228 treatment effectively inhibited the formation of focal adhesions and impaired spreading in human fibroblasts. Additionally, cell motility (FIG. 3c) and contraction/α-SMA expression (FIG. 3d-e) were all decreased with FAK inhibition. Together, these findings suggest that small molecule therapies targeting FAK can potentially impact human fibrotic disease.

We then examined how these early intracellular events were connected with pro-fibrotic pathways in human tissues. In vitro, both mechanical and inflammatory stimuli induced robust MCP-1 secretion (FIG. 3f). When both stimuli were applied simultaneously, there was a potentiating effect on MCP-1 secretion. Small molecule blockade of FAK was sufficient to prevent either stimulus from activating MCP-1

(FIG. 3f), suggesting that FAK is a critical node in chemokine signaling. Moreover, inhibition of ERK (but not Akt, p38 or JNK) blocked strain-induced MCP-1 release (FIG. 3g), highlighting the importance of the FAK-ERK-MCP1 axis in mechanotransduction and inflammation.

Figure 4:
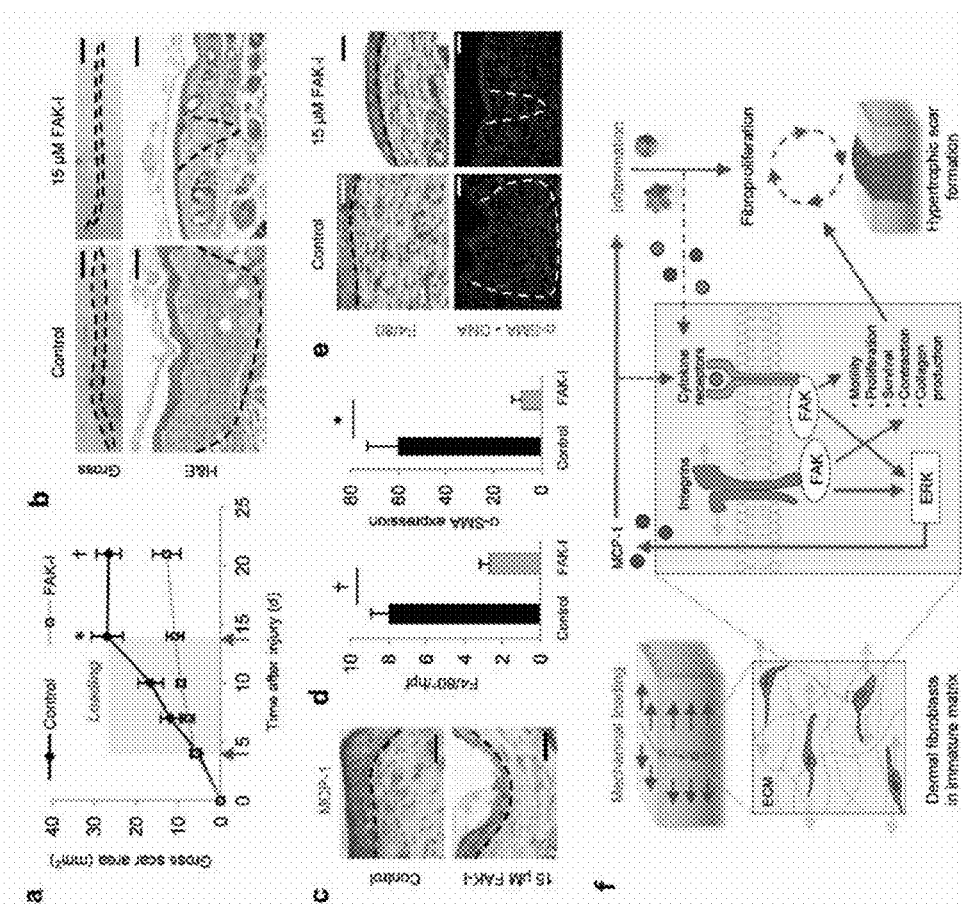
FIG. 4 Intradermal PF573228 treatment. (a) Surface scar formation with 15 μM PF573228 treatment. n=6. (b) Images of post-injury day ten scars. Scar within dashed line. Scale bar 0.25 cm (top), 100 μm micrographs. n=6. (c) Mcp-1 immunolocalization (purple color). Dashed line indicates basement membrane. Scale bar 50 μm. (d) Quantification and (e) micrographs of F4/80$^+$ macrophages and α-SMA expression. n=6. Scale bar 50 μm top; 100 μm bottom. Values represent means±s.e.m.; *p<0.01, †p<0.05. (f) Schematic of proposed "vicious cycle" of hypertrophic scarring driven by mechanical activation of local and systemic fibroproliferative pathways via fibroblast FAK.

To evaluate the therapeutic potential of small molecule anti-FAK therapies, we administered PF573228 daily to cutaneous wounds in the HTS model. Consistent with the in vitro and FAK KO data, pharmacologic blockade of FAK significantly reduced scar formation in vivo (FIG. 4a). In post-injury day ten scars, FAK inhibition reduced gross scar area by 170% versus control (p=0.003) (FIG. 4b) and attenuated scar matrix density. Additionally, epithelial thickness, epithelial proliferation and dermal proliferation were attenuated by 35% (p=0.004), 57% (p<0.001) and 28% (p=0.01), respectively. PF573228 treatment also significantly decreased the mechanical activation of ERK and importantly, MCP-1-associated pathways were blocked, replicating the phenotype observed in the transgenic mice.

In addition to these chemokine-mediated mechanisms, FAK might also control fibrosis by directly activating fibroblast collagen production, explaining the marginal increase in fibrosis in loaded MCP-1 KO wounds. In vitro, inhibition of FAK or ERK significantly blocked collagen production in human fibroblasts with the ratio of collagen I (thicker): collagen III (thinner) gene expression decreased by 18% (p=0.076). Similarly, the ratio of collagen I:III expression was reduced by 34% (p=0.040) and 51% (p=0.036) in FAK KO and FAK inhibitor-treated scars, respectively, corroborating the histologic analyses that demonstrated a paucity of scar matrix with FAK blockade. This suggests that a minor secondary effect of FAK mechanotransduction is direct modulation of collagen fibrillogenesis, as previously described in the kidney.

Based on these studies, we propose a model for load-induced fibrosis whereby mechanical force activates both MCP-1 secretion and collagen production via FAK to perpetuate a "vicious cycle" of fibroproliferation post-injury (FIG. 4f). Although other mechanoresponsive cell types and cytokines are undoubtedly involved in scar mechanotransduction, these findings collectively provide for the first time an important framework to understand how mechanical stimuli trigger local and systemic responses to induce scar hypertrophy. More broadly, these results suggest that targeted strategies to uncouple mechanical force from inflammation and fibrosis may prove clinically successful across diverse organ systems.

Methods

Mice. The Administrative Panel on Laboratory Animal Care at Stanford University approved all procedures. We generated transgenic mice with fibroblast-restricted FAK deletion by crossing fibroblast-specific procollagen-α2(I) Cre recombinase mice to homozygous floxed FAK mice (B6.129-Ptk2$^{tm1Lfr}$/Mmcd, purchased from UC Davis MMRRC). We backcrossed mice at least eight generations on a C57BL/6 background and identified transgenic progeny using published methods. Tamoxifen induction was performed via daily intraperitoneal injections for five days one week before wounding. We used female mice aged 8-12 weeks for all experiments; FVB/NJ and MCP-1 KO (B6.129S4-Ccl2$^{tm1Rol}$) mice were purchased from The Jackson Laboratory (Bar Harbor, Me.).

Microarray. We harvested wildtype murine tissue at day six or 14 post-injury following 48 hours or ten days of mechanical loading, respectively (n=4 mice per group per time point). RNA was hybridized to the GeneChip microarray (Affymetrix, Santa Clara, Calif.). We analyzed data using GeneSpring GX 11.0 (Agilent Technologies Inc., Santa Clara, Calif.) and the Significance Analysis of Microarray toolkit in Microsoft Excel (Microsoft, Redmond, Wash.). We performed hierarchical clustering in MATLAB (The MathWorks, Inc., Natick, Mass.). We constructed pathway networks using Ingenuity Pathways Analysis (Ingenuity Systems, Redwood City, Calif.).

Fibroblast harvest. We isolated primary dermal mouse fibroblasts after overnight incubation in trypsin (Gibco/Invitrogen, Carlsbad, Calif.) followed by 1 mg mL$^{-1}$ Liberase TL (Roche, Indianapolis, Ind.). We obtained human fibroblasts from fresh tissue specimens following IRB-approved protocols at Oregon Health and Sciences University. We incubated specimens overnight in 5 mg mL$^{-1}$ dispase (Roche) followed by 0.5 mg mL$^{-1}$ collagenase type I (Roche) and 0.2 mg mL$^{-1}$ trypsin. We used human cells from passages four to eight.

In vitro strain studies. We applied equibiaxial static strain to human fibroblasts as previously published (Wang, et al. J Cell Physiol 206, 510-517 (2006)). After 24 hours of strain, we collected media for CCL2/MCP-1 ELISA (R&D Systems, Inc., Minneapolis, Minn.) or Sircol total collagen assay (Biocolor Ltd., Carrickfergus, Northern Ireland). Commercially available small molecules were dissolved in dimethylsulfoxide (DMSO, Sigma-Aldrich, St. Louis, Mo.) and used to target FAK (PF573228, Tocris Biosciences, Bristol, United Kingdom), Akt (LY294002), ERK (PD98059), p38 (SB203580) and JNK (SP600125). PDGF (10 ng mL$^{-1}$) was used for ligand activation of FAK. We purchased all molecules from Sigma-Aldrich unless otherwise noted.

Live/dead assay. We used a live/dead assay (Calbiochem/EMD Chemicals Inc., Gibbstown, N.J.) after 24 hours of exposure to PF573228 in vitro.

In vitro wound healing. We assessed fibroblast motility using a scratch migration assay, Aarabi, et al. *FASEB J* 21, 3250-3261 (2007).

Fibroblast-populated collagen lattices. We performed fibroblast contraction studies as previously published, Ehrlich, *Methods Mol Med* 78, 277-291 (2003).

Murine HTS model. We used a murine HTS model as previously published by our group, Aarabi, et al., supra.

Microscopy and immunohistochemistry. We incubated paraformaldehyde-fixed cells with primary antibody (pFAK-Y397 or FAK 1:200, BD Biosciences, San Jose, Calif.) followed by AlexaFluor488-conjugated secondary antibody (Molecular Probes/Invitrogen). We performed cytoskeletal staining with phalloidin-AF488 or Cy3-conjugated antibody against α-SMA (Sigma-Aldrich). We performed H&E, picrosirius red and trichrome staining (Sigma-Aldrich) on paraffin-embedded sections. We used primary antibodies against FAK, MCP-1, F4/80, Ki67, and α-SMA. Immunostaining was developed with VIP, NovaRed or diaminobenzidine (Vector Laboratories, Burlingame, Calif.), or secondary fluorescent antibodies AF488 or AF594. We performed apoptotic staining using the In Situ Cell Death Detection Kit (Roche). We purchased all antibodies from Abcam Inc. (Cambridge, Mass.) unless otherwise noted. We processed images for publication using Adobe Photoshop CS3 (Adobe Systems Incorporated, San Jose, Calif.) and two blinded investigators performed image quantification using ImageJ (NIH, Bethesda, Md.).

Gene expression. We performed qPCR as previously published. We used Taqman Gene Expression Assays (Applied Biosystems, Foster City, Calif.) for in vitro qPCR.

In situ hybridization. We amplified the MCP-1 template from mouse cDNA by PCR using sequence-specific primers including the T7 or T3 RNA promoter region to make anti-sense and sense probes, respectively. We transcribed Riboprobe in the presence of Digoxigenin-11-dUTP (Roche) which was detected using the DIG Nucleic Acid Detection Kit (Roche).

Immunoblotting. We performed immunoblotting as previously described. We used the following antibodies: FAK (BD Biosciences), p-FAK Y397, p-FAK S732, p-ERK T202/Y204 and ERK, p-Akt S473 and Akt (Cell Signaling Technology, Inc., Danvers, Mass.), p-p38 Y182 and p38, p-JNK T183/Y185 and JNK, MCP-1 and β-actin. We obtained all antibodies from Abcam Inc. unless otherwise noted.

Intradermal injections. We administered intradermal injections (300 µL) of DMSO, 15 µM PF573228, or 150 µM PF573228 to unwounded murine skin or unloaded incisions. For HTS model experiments, we injected 15 µM PF573228 or recombinant mouse Mcp-1 (1 µg mL$^{-1}$, R&D Systems Inc.) daily between days 4 and 14 post-injury.

Flow cytometry. We digested post-injury day ten scars and incubated them with rat monoclonal antibodies against F4/80 (eBioscience, San Diego, Calif.) and CCR2 (R&D Systems Inc.) as previously described.

Statistical analysis. We performed statistical analysis using Student's unpaired t-test or one way ANOVA for multiple comparisons (MATLAB). Values are represented as means±s.e.m. P values <0.05 are considered statistically significant.

What is claimed is:

1. A method of reducing scarring during healing of a skin wound, comprising:
    administering to a subject with a skin wound a pharmaceutical formulation comprising an effective dose of an FAK inhibitor selected from: PF-573,228, PF-562,271, FAK Inhibitor 14, a 2,4,DI (hetero-) arylamino (-oxy)-5-substituted pyrimidine, a derivative of a 5-substituted 2,4-diaminopyridine, and a combination thereof; for a period of time sufficient to reduce scarring as compared to a healed wound of an untreated subject.

2. The method of claim 1, wherein the FAK inhibitor is selected from: PF-573,228 and FAK Inhibitor 14.

3. A method of reducing scarring during healing of a skin wound, comprising:
    administering to a human subject with a skin wound a pharmaceutical formulation comprising: (i) an effective dose of an FAK inhibitor selected from: PF-573,228, FAK Inhibitor 14, and a combination thereof; and (ii) one or both of an antibiotic and a non-steroidal anti-inflammatory drug,
    for a period of time sufficient to reduce scarring by at least about 25% relative to a healed wound of an untreated subject.

* * * * *